United States Patent [19]

Zimakova et al.

[11] Patent Number: 4,571,403
[45] Date of Patent: Feb. 18, 1986

[54] ANTIANGINAL MEDICATED COMPOUND

[75] Inventors: Irina E. Zimakova; Dania A. Valimukhametova; Irina V. Zaikonnikova; Vladimir F. Bogoyavlensky, all of Kazan; Natalya V. Kaverina, Moscow; Roman A. Kamburg; Anatoly M. Karpov, both of Kazan; Lenor I. Khmelnitsky, Moscow; Oleg V. Lebedev, Moscow; Lia V. Epishina, Moscow; Lidia V. Lapshina, Moskovskaya; Ljudmila I. Suvorova; Nikolai V. Darinsky, both of Moscow, all of U.S.S.R.; Sergei S. Novikov, deceased, late of Moscow, U.S.S.R., by Valentina V. Sevostyanova, Alexandr S. Novikov, Sergei S. Novikov, administrators

[73] Assignee: Institut Organicheskoi Khimii Imeni N.D. Zelinskogo Akademii Nauk SSSR, Moscow, U.S.S.R.

[21] Appl. No.: 678,698

[22] Filed: Dec. 6, 1984

[51] Int. Cl.$^4$ .......................................... A61K 31/415
[52] U.S. Cl. ..................................... 514/387; 514/929
[58] Field of Search ...................... 424/273 R; 514/387

[56] References Cited
PUBLICATIONS

Chem. Abstr. 97: 104,040g, 1982.
Chem. Abstr. 98: 83,542a, 1983.
Kaverina et al., Cardiology, Monthly Jour. Med. Moscow, vol. XV, No. 7, Oct. 1961.
Kaverina et al., Cardiology, Monthly Jour. Med. Moscow, vol. XI, No. 11.

Primary Examiner—Albert T. Meyers
Assistant Examiner—John W. Rollins, Jr.
Attorney, Agent, or Firm—Ladas & Parry

[57] ABSTRACT

The anginal medicated compound according to the present invention comprises the active principle 2,4,6,8-tetramethyl-2,4,6,8-tetraazobicyclo-/3,3,0/-octanedione-3,7 of the formula:

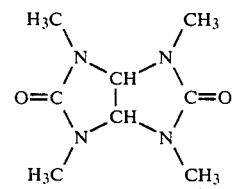

in combination with a pharmaceutical carrier.

The medicated compound according to the present invention is useful for the treatment of patients suffering from ischemic heart disease.

4 Claims, No Drawings

ANTIANGINAL MEDICATED COMPOUND

This is a continuation of co-pending application Ser. No. 467,307 filed on Feb. 17, 1983, now abandoned.

FIELD OF THE INVENTION

The present invention relates to the art of medicine and, more specifically, to a novel antianginal medicated compound.

BACKGROUND OF THE INVENTION

Well known in the art are antianginal medicated compounds such as alcohol nitrates, for example trinitroglycerol. Trinitroglycerol increases the general coronary blood flow, selectively increases blood flow in endocaridal zones of ischemized myocardium, selectively suppresses the vascular component of the acute (primary) pain reaction, causes no substantial intensification of contractability of the heart (inotropic effect) and results in an insignificant hypotension of the systemic arterial pressure. However, nitroglycerol has certain side effects such as bad tolerance of the preparation by certain categories of patients accompanied by strong headaches and incompatibility with some other pharmaceutical preparations.

Known in the art are such preparations as cardaron [2-butyl-3-benzofuranyl]-[4-(2-diethylaminoethoxy)-3,5-diodophenyl]ketone hydrochloride (cf. N. V. Kaverina et al. "Kardiologiya", 1971, 11,II,96) and the preparation referred to as nonachlazine (10-$\beta$/1,4-diazobicyclo-4,3,0)-nonanyl-2-chlorophenothiazine) (N. V. Kaverina et al. "Kardiologiya", 1975, 7.43).

These prior art preparations are the closest relative to that of the present invention as regards its pharmacological effect.

Cardaron relates to antiadrenergic preparations with a mixed effect; it has a negative inotropic effect on myocardium. Cardaron possesses no selective effect on blood supply of the ischemized zone of myocardium. Furthermore, cardaron can cause side phenomena in the form of affection of eye cornea. This preparation has a narrow therapeutic range and a short duration of its action.

The preparation nonachlazine possesses $\beta$-adrenostimulating component of the effect on myocardium. This preparation causes a lasting hypertension of the arterial pressure. It has certain contraindications (cannot be administered in the case of kidney and liver diseases).

The antianginal medicated preparation according to the present invention has not been hitherto described in the literature.

SUMMARY OF THE INVENTION

It is an object of the present invention to provide a novel antianginal medicated compound.

This object is accomplished by that the preparation according to the present invention possessing antianginal effect and comprising an active principle and a pharmaceutical carrier, contains as the active principle 2,4,6,8-tetramethyl-2,4,6,8-tetraazobicyclo-/3,3,0/-octanedione-3,7 of the following chemical formula:

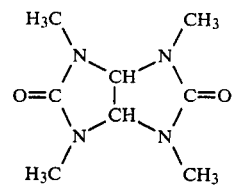

The medicated compound according to the present invention possesses the antianginal effect and is useful for the treatment of ischemic heart disease.

The preparation according to the present invention can be used in different preparative forms. It should be preferably used as tablets and liquids for injections. The medicated compound in the form of tablets should preferably contain 0.3 g of the active principle per tablet. As the pharmaceutical carrier for injection solutions it is advisable to use bidistilled water. The injection solutions contain 10% by weight of the active principle.

DETAILED DESCRIPTION OF THE INVENTION

The active principle of the medicated compound according to the present invention, i.e. 2,4,6,8-tetramethyl-2,4,6,8-tetraaazobicyclo-/3,3,0/-octadione-3,7 comprise a white crystalline powder with a bitter taste, a weak amide odour, well soluble in water.

Antianginal properties of the medicated compound according to the present invention have been studied in the experiment on animals and in clinical tests.

The acute toxicity of the preparation according to the present invention has been studied on mice and rats. It has been found that the preparation is low-toxic: $LD_{50}$ for mice is 3,800 mg/kg of the body weight, for rats—3,450 mg/kg. The study of chronical toxicity in experiments on rats in intraperitoneal administration in the dose of 200 mg/kg for 6 months and in the dose of 1,000 mg/kg for 1 month has shown that the preparation is not accumulated, it does not affect hematoplasty and urination. Histological investigations revealed no pathological changes in the visceral organs (kidney, liver, spleen, heart and the like).

The effect of the preparation on the arterial pressure has been also studied. In experiments on cats (23 tests) and dogs (16 tests) it has been found that the preparation when administered in the dose of 50 mg/kg intravenously exerts no essential effect on the systemic arterial pressure causing uncertain hypertensive reaction during the first 5 minutes after the administration of the preparation. When administered in doses of 250 mg/kg, the preparation causes opposite-sign changes of the arterial pressure mainly of hypotensive character. The average value of the maximum drop of pressure during the first 10 minutes after the administration is 8–10% of the initial level. In doses of 500 mg/kg the preparation causes hypotensive reaction with the intensity of 15–18% of the initial level at the duration of the effect of 20–30 minutes. The preparation does not change the character of pressor reactions of arterial pressure on noradrenaline (3 $\mu$g/kg) and of depressor reactions on isoproterenol (2.5 $\mu$g/kg). Hence, it may be conducted that the preparation does not influence the adrenoreactive structures of the vessels.

In tests on cats (11 tests) under the general anesthesia conditions (urethane+chloralose) the rate of coronary blood flow is measured by the blood outflow from the coronary sinus following the method suggested by N. V. Kaverina /1963/. At the same time, the content of oxyhemoglobin in the coronary venous blood is determined by the photometrical method and the absorption of oxygen by myocardium is calculated on the basis of the arterio-venous difference value.

It has been found that the preparation improves heart blood supply even when administered in the dose of 50 mg/kg intravenously increasing coronary blood flow by $32\pm5\%$ on the average. The effect duration varies within the range of from 5 to 10 minutes. With increasing the preparation dose up to 500 mg/kg, the intensity and duration of the effect are increased reaching respectively $108\pm12\%$ and 30–40 minutes.

Simultaneously with increasing coronary blood flow, the preparation causes decrease in the arterio-venous difference relative to oxygen due to an increased content of oxyhemoglobin in coronary venous blood. Calculation of the amount of the heart-absorbed oxygen points to it explicit increase ($29\pm2.3\%$). However, it should be noted that the increase of coronary blood flow under the action of the preparation according to the present invention surpasses the the absorption of oxygen by myocardium, wherefore it can be suggested that the preparation provides favourable conditions for the supply of oxygen to myocardium tissues.

To find out the participance of the vascular factor in redistribution of regional blood flow, resistogram of vessels of heart, kidney and limbs has been recorded. It has been found that the preparation monodirectionally lowers tension of all vessels, through the resistance of coronary vessels is lowered to a greater extent than that of peripheral vessels. The effect of the preparation on the heart activity and basic characteristics of hemodynamics has been also studied.

In experiments on cats and dogs under the general anesthesia conditions the volumetric flow rate of blood flow in the ascending part of the aortic arch has been recorded by the electromagnetic method using an electromagnetic blood flow meter and vessel sensors of appropriate size. On the basis of analysis of the phase curve of the blood flow, the main characteristics of heart activity and hemodynamics have been calculated. It has been found that when administered in doses of 200–500 mg/kg intravenously, the preparation considerably (50–70%) and lastingly (during 30–40 minutes) increases blood flow in aorta against the background of an uncertainly pronounced tachycardia. The averaged data of analysis of phase curves of the blood flow in cat's aorta under general anesthesia conditions (8 tests) are given in the Table hereinbelow. It can be seen from the Table that the preparation is capable of increase the heart function which is revealed by increasing impact outflow of blood along with a reduced time of left ventricle systole, as well as by increasing of the maximum (peak) aortic blood flow, maximum acceleration imparted to blood by contracting left ventricle and intensified heart activity.

Also studied has been the effect of the medicated compound of the present invention on processes of central regulation of blood circulation.

In experiments on anesthetized (urethane+chloralose) and immobilized (succinylcholine bromide) cats (14 tests) there has been studied the effect of the preparation in various doses on the tonic and reflectorial bioelectric activity in sympathetic nerves of heart and kidney. Somatosympathetic reflexes are caused by electric irritation of afferent A- and C- fibers of the tibial nerve.

It has been found that when administered in low doses (50 mg/kg) does not noticeably change the character and intensity of tonic and reflectorial activity in sympathetic nerves. In a certain number of the experiments one could observe a slight amplification of spontaneous activity and facilitation of reflectorial responses which is manifested in an increased amplitude and duration of A-responses and, especially, C-responces. The value and character of pressor responses caused by a tetanic irritation of tibial nerve remain unchanged.

When administered in high doses (250–500 mg/kg) the preparation results in amplification of the inhibiting component of the reflectorial response, which can be assessed by a longer duration of the post-discharge inhibition of the spontaneous activity. In addition, there were suppressed C - resonses of the reflectorial discharges. Tonic activity was but weakly inhibited.

TABLE

Effect of the preparation (250 mg/kg intravenously) on the activity of heart and basic characteristics of hemodynamics

| No. | Hemodynamics characteristics | Background |
|---|---|---|
| 1 | Average arterial pressure, mm Hg | $148 \pm 7.6$ |
| 2 | Pulse frequency, b/min | $181 \pm 5$ |
| 3 | Time of systolic ejaculation, seconds | $0.14 \pm 0.008$ |
| 4 | Time of diastolic relaxation, seconds | $0.22 \pm 0.01$ |
| 5 | Systolic (beat) volume, ml | $1.93 \pm 0.12$ |
| 6 | Minute volume, ml/min | $372 \pm 26$ |
| 7 | Maximum blood flow | $19.7 \pm 2.1$ |
| 8 | Maximum linear speed, cm/sec | $35 \pm 1.9$ |
| 9 | Maximum acceleration, cm/sec | $861 \pm 42$ |
| 10 | Minute work, kgm | $0.88 \pm 0.09$ |

| Time after administration, minutes | | | |
|---|---|---|---|
| 5 | 10 | 20 | 40 |
| $137 \pm 6.9$ | $126 \pm 8.1$ | $139 \pm 7.4$ | $146 \pm 8.8$ |
| $190 \pm 6$ | $197 \pm 5$ | $191 \pm 7$ | $183 \pm 7$ |
| $0.12 \pm 0.01$ | $0.11 \pm 0.09$ | $0.13 \pm 0.01$ | $0.13 \pm 0.008$ |
| $0.22 \pm 0.01$ | $0.21 \pm 0.01$ | $0.20 \pm 0.01$ | $0.23 \pm 0.009$ |
| $2.22 \pm 0.15$ | $2.34 \pm 0.18$ | $2.01 \pm 0.15$ | $1.97 \pm 0.12$ |
| $464 \pm 38$ | $488 \pm 43$ | $415 \pm 32$ | $397 \pm 33$ |
| $30 \pm 8.2$ | $34 \pm 2.6$ | $28 \pm 1.4$ | $21.4 \pm 2.2$ |
| $41 \pm 2.7$ | $49 \pm 2.8$ | $38 \pm 2.3$ | $33. \pm 3.1$ |
| $1032 \pm 67$ | $1108 \pm 83$ | $890 \pm 49$ | $844 \pm 51$ |
| $1.12 \pm 0.15$ | $1.23 \pm 0.11$ | $0.97 \pm 0.08$ | $0.83 \pm 0.10$ |

These facts demonstrate that the preparation according to the present invention is capable of interference into processes of central regulation of blood circulation which, in turn, can be an important link in the mechanism of its antianginal action.

The effect of the preparation on the functional state of the ischemic center has been studied in experiments on dogs under the conditions of general anesthesia. The effects caused by the preparation have been studied on the model of an acute attack of stenocardia (Sekeresh's model). The functional state of the ischemic focus has been assessed through analysis of epicardial heart electrograms in the ischemic zone and adjacent regions. The stenocardiac attack is caused by way of a partial occlusion of the coronary artery (left descending artery) and including a high rythm of heart contractions (up to 250 beats/minute) by way of electrical stimulation of the heart auricula. Under these conditions there take place changes of the heart electrograms typical for acute ischemia of myocardium. When administered in the dose of 200 mg/kg, the preparation inhibited the development of ischemic changes of epicardial electrograms in the zone of ischemia. Futhermore, the study of the preparation effect on the retrograde blood flow from the ischemic zone has shown that the preparation is capable of considerably increase the blood inflow into the ischemic zone due to amplification of colateral blood flow in endocardial layers of the ischemized myocardium.

As it can be judged from the experimental model of acute myocardium ischemia, the medicated compound according to the present invention is more active (as regards the sum of pharmacological effects) than the known preparation nonachlazine which is demonstrated by improvement of the functional state of the ischemic zone of myocardium and efficiency of selective blood supply of the ischemic zone.

The preparation according to the present invention can be characterized (as regards the whole of the cardio-vascular effects caused thereby as revealed by the results of the experiments performed) as the preparation with pronounced antianginal properties. The preparation is capable of improve the functional state of the ischemic centre by lowering the content of lactate in the blood outflowing from the ischemic zone. It increases contractibility of myocardium, causes no substantial change of arterial pressure and suppresses the vascular component of pain reactions.

The preparation according to the present invention has been also tested under clinic conditions.

There were studied 84 patients aged 29 to 77 (46 men and 38 women) suffering from ischemic heart disease.

The patients with ischemic heart disease were classified by stages: stage 1–18 persons, stage 2–40 persons, stage 3–4 persons (according to L. I. Fogelson, 1972). In 46 patients there was the attendant hypertonic disease of the second stage.

The remoteness of the disease was varied from 6 months to 22 years. The preparation was administered perorally in doses of 0.6–0.9 g 3–4 times a day. The daily dose is 1.8–3.6 g. The treatment course was 7 to 60 days; after a 5–7 days' interval the treatment was resumed depending on its efficiency so that the total course duration was up to 6 months. The effectiveness of the treatment was evaluated by the dynamics of complaints, clinic chart, objective data of pulse and arterial pressure, electrocardiographic and biochemical characteristics.

In patients with ischemic disease the frequency and intensity of stenocardia attacks were reduced, the electrogram showed rhythm normalization, amelioration of metabolic processes.

In patients with the attendant hypertonic disease, amelioration of the condition was observed at the 2–5-th day along with reduction of arterial pressure from maximum of 180.8±3.9 mm Hg to 161.4±3.8 mm Hg, minimal from 102.2±1.2 mm Hg to 89.7±4.0 mm Hg, and pulse normalization.

There were found certain changes in bio chemical and clinic blood characteristics: increase of the number of erythrocytes from 4.6±0.3 mln to 5.3±0.3 mln in mm$^3$, hemoglobin from 82.7±2.6% to 86.3±3.2%, leucocytes from 5,520±499 in mm$^3$ to 6,080±221 in mm$^3$. There was the trend of increasing content of lymphocytes from 26.9±1.2% to 31.0±2.8%, the content of total protein was increased from 7.73±0.1% to 8.65±0.25%. In the proteinogram there was noted a small increase in gamaglobulins from 19.87±1.83% to 22.54±2.31%; in the remaining fractions there were insignificant opposite-sign variations, in the electrolytic balance—a proven increase of potassium in erythrocytes from 65.7±5.7 mequiv/l to 80.2±5.2 mequiv/l, uncertain decrease of potassium in plasma from 3.82±0.16 mequiv/l to 3.45±0.08 mequiv/l, the content of sodium in erythrocytes and plasma was not substantially changed. The content of prothrombin during the treatment course was not changed, that of cholesterol was positevely lowered from 294.0±16.4% to 245±15.0 mg %.

In general, a good therapeutic effect was observed in 77% of the patients.

The results of the above-described tests allow the following conclusions characterizing the properties of the medicated compound according to the present invention.

1. It possesses a low toxicity - LD$_{50}$ for mice is 3,800 mg/kg of body weight, for rats - 3,450 mg/kg of body weight.

2. The preparation has a wide range of effective doses (50 to 1,500 mg/kg).

3. It increases the volumetric rate of total coronary blood flow, lowering the arterio-venous difference relative to oxygen.

4. It is capable of improving functional state of the ischemic centre, while lowering the content of lactate in the blood outflowing from the ischemic zone.

5. It contributes to the development of the colateral blood flow in deep (endocardial) layers of myocardium, i.e. it enhances the blood supply of the predominantly injured regions of myocardium.

6. It is capable of inhibiting the sympathetic tonus of heart and vessels, as well as vascular components of pain reactions.

7. It provides a positive inotropic effect without affecting the frequency of heart contractions, thus making it possible to recommend this preparation for the treatment of patients suffering from ischemic heart disease and cardiac insufficiency.

The medicated compound according to the present invention can be used in different preparative forms (tablets, injection solutions, suppositoria and the like).

It is preferable to use tablets with the content of the active principle of 0.3 g in each tablet. The tabletted preparation is administered in the dose of 1-2 tablets thrice a day (each tablet containing 0.3 g of the active principle). The preparation according to the present invention can be used as injection solutions, preferably 10% ones. The 10% solution of the preparation is injected intravenously in an amount of from 4 to 10 ml during 10 minutes.

No contraindications against the administration of the preparation have been revealed. Side effects are absent. The medicated compound according to the present invention should be stored at room temperature in a dark place, list B.

The medicated compound according to the present invention in the form of various preparative forms is obtained by conventional methods. The active principle of the medicated compound according to the present invention comprises 2,4,6,8-tetramethyl-2,4,6,8-tetraazobicyclo-/3,30/-octanedione-3,7 which is prepared by reacting N,N' -dimethylurea with glyoxal in an aqueous acidic medium upon heating to a temperature within the range of from 90° to 95° C., followed by isolation of the desired product by way of azeotropically distilling-off water and recrystallization of the product.

What is claimed is:

1. A method for the treatment of patients suffering from ischemic heart disease comprising administering to said patient an effective amount of 2,4,6,8-tetramethyl-2,4,6,8 tetraazobicyclo-(3,3,0)-octanedion-3,7.

2. A method as claimed in claim 1 comprising administering tablets containing the active principle in the amount of 0.3 g per tablet.

3. A method as claimed in claim 1 comprising administering injection solutions containing the active principle in the amount of 10% by weight.

4. A method as claimed in claim 1 comprising administering injection solutions containing bidistilled water as the pharmaceutical carrier.

* * * * *

UNITED STATES PATENT AND TRADEMARK OFFICE
CERTIFICATE OF CORRECTION

PATENT NO. : 4,571,403
DATED : February 18, 1986
INVENTOR(S) : ZIMAKOVA, Irina E. et al It is certified that error appears in the above-identified patent and that said Letters Patent is hereby corrected as shown below:

Page 1, assignee information [73], please insert after "Institut Organicheskoi Khimii Imeni N.D. Zelinskogo Akademii Nauk SSSR, Moscow, U.S.S.R." -- and Kazansky Meditsinsky Institut Imeni S.V. Kurashova, Kasan, U.S.S.R.

Page 1, after "[21] Appl. No.: 678,698", please insert -- Related U.S. Application Data [63] Continuation of Ser. No. 467,307, February 17, 1983, abandoned -- column 1, after the first sentence after the title, insert -- This is a continuation of co-pending application Ser. No. 467,307, filed on February 17, 1983, now abandoned. --

Signed and Sealed this

Twenty-fourth Day of June 1986

[SEAL]

Attest:

DONALD J. QUIGG

Attesting Officer

Commissioner of Patents and Trademarks